United States Patent
Greenberg et al.

(10) Patent No.: US 6,723,321 B2
(45) Date of Patent: *Apr. 20, 2004

(54) AUTOINDUCER SYNTHASE MODULATING COMPOUNDS AND USES THEREOF

(75) Inventors: E. Peter Greenberg, Iowa City, IA (US); John E. Cronan, Jr., Urbana, IL (US); Bryce V. Plapp, Iowa City, IA (US); Matthew R. Parsek, Iowa City, IA (US)

(73) Assignees: The Board of Trustees of the University of Illinois, Urbana, IL (US); The University of Iowa Research Foundation, Iowa City, IA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/227,488

(22) Filed: Jan. 6, 1999

(65) Prior Publication Data

US 2003/0054512 A1 Mar. 20, 2003

Related U.S. Application Data (60) Provisional application No. 60/094,988, filed on Jul. 31, 1998.

(51) Int. Cl.[7] .............. A61K 39/00; A61K 39/02; C12P 19/34; C12P 15/64; C12N 1/20
(52) U.S. Cl. .............. 424/185.1; 424/185.1; 424/190; 424/832; 435/91.32; 435/91.4; 435/91.41; 435/91.52; 435/93.4; 435/252.3; 530/300; 530/305; 536/23.1; 935/9; 935/10; 935/13; 935/14; 935/16; 935/19; 935/22; 935/23; 935/24; 935/27; 935/88
(58) Field of Search .............. 424/185.1, 190, 424/832; 435/91.32, 91.4, 91.41, 91.52, 93.4, 252.3; 530/300, 305; 536/23.1; 935/9, 10, 13, 14, 16, 19, 22, 23, 24, 27, 88

(56) References Cited

U.S. PATENT DOCUMENTS 5,591,872 A    1/1997   Pearson et al. ............. 549/321

FOREIGN PATENT DOCUMENTS

WO      WO 97/11690       4/1997

OTHER PUBLICATIONS

Hwang, I. et al. "TraI, a LuxI homologue is responsible from production of conjugation factor, the Ti plasmid N–acylhomoserine lactone autoinducer" *Proc. Natl. Acad. Sci. U.S.A.* 91:4639–4643 (May 1994).

Parsek, M. et al. "Acyl homoserine–lactone quorum–sensing signal generation" *Proc. Natl. Acad. Sci. U.S.A.* 96:4360–4365 (Apr. 1999).

(List continued on next page.)

*Primary Examiner*—Lynette R. F. Smith
*Assistant Examiner*—Jana Hines
(74) *Attorney, Agent, or Firm*—DeAnn F. Smith, Esq.; Elizabeth A. Hanley, Esq.; Lahive & Cockfield, LLP (57) ABSTRACT

Provided are compositions and methods useful for modulating the activity of autoinducer synthase catalysts. A method for identifing modulators of the autoinducer synthesis reaction is also provided. Such modulators are useful for controlling bacterial growth and can be used for therapeutic treatment of bacterial infections particularly in immunocompromised subjects. They are also useful in treating disease states associated with autoinducer synthesis and biofilm development.

32 Claims, 1 Drawing Sheet

OTHER PUBLICATIONS

Robson, N. et al. "Bacterial N–acyl–homoserine–lactone–dependent signalling and its potential biotechnological applications" *Trends in Biotechnology* 15(11):458–464 (Nov. 1997).

Val, D. et al. "In vivo evidence that S–adenosylmethionine and fatty acids synthesis intermediates are the subtrztes for the LuxI family of autoinducer synthases" *Journal of Bacteriology* 180(10):2644–2651 (May 1998).

Baldwin, T.O. et al., "The complete nucleotide sequence of the lux regulon of *Vibrio fischeri* and the luxABN region of *Photobacterium leignathi* and the mechanism of control of bacterial bioluminescence," *J. of Biolum. and Chemilum.* 4:326–341 (1989).

Bassler, B.L. et al., "Intracellular signaling in *Vibrio harveyi:* sequence and function of genes regulating expression of luminescence," *Mol. Microbiol.* 9:773–786 (1993).

Brint, J.M. et al. "Synthesis of multiple exoproducts in *P. aeruginosa* is under control of RhlR–RhlI another set of regulators in strain POAI with homology to the autoinducer responsive LuxR–LuxI family," *J Bacteriol.* 177:7155–7163 (1995).

Davies, D.G. et al., "The involvement of cell–to–cell signals in the development of a bacterial biofilm," *Science.* 280:295–298 (1998).

Devine, J.H. et al. "Identification of the operator of the lux regulon from *Vibrio fisheri* strain ATCC 7744," *Proc. Natl. Acad. Sci. USA* 86:5688–5692 (1989).

Eberhard, A. et al. "Structural identification of autoinducer of *Photobacterium fisceri* luciferase," *Biochemistry.* 20:2444–2449 (1981).

Eberhard, A. et al. "Synthesis of the lux gene autoinducer in *Vibrio fischeri* is positively autoregulated," *Arch. of Microbiol.* 155:294–297 (1991).

Engebrecht, J. et al. "Bacterial biolumnecense; isolation and genetic analysis of the functions from *Vibrio fischeri,*" *Cell.* 32:773–781 (1983).

Fuqua, W.C. et al. "A LuxR–LuxI type regulatory system activates Agrobacterium Ti plasmid conjugal transfer in the presence of a plant tumor metabolite," *J. Bacteriol.* 176:2796–2806 (1994).

Fuqua, W.C. et al. "Census and consensus in bacterial ecosystems: the LuxR–LuxI family of quorum sensing transcriptional regulators," *Annu. Rev. Microbiol.* 50:727–751 (1996).

Gilson, L. A. et al. "AinS and a new family of autoinducer synthesis proteins," *J. Bacteriol.* 177:6946–6951 (1995).

Gray, K.M. et al,. "Physical and functional maps of the luminescence gene cluster in an autoinducer–deficient *Vibrio fischeri* isolated from a squid light organ," *J. Bacteriol.* 174:4384–4390 (1992).

Hanzelka, B.A. et al. "Evidence that the N–terminal region of *Vibrio fischeri* LuxR protein constitutes and autoinducer binding domain," *J Bacteriol.* 177:815–817 (1995).

Hanzelka, B.A. et al. "Quorum sensing in *Vibrio fischeri:* evidence that S–adenosyl methionine is the amino acid substrate for autoinducer synthesis," *J. Bacteriol.* 178:5291–5294 (1996).

Huisman, G.W. et al. "Sensing starvation: a homoserine lactone dependent signaling pathway in *Escherichia coli,*" *Science.* 265:537–539 (1994).

Kaplan, H.B. et al. "Diffusion of an autoinducer is involved in regulation of *Vibrio fischeri* luminescence system," *J. Bacteriol.* 163:1210–1214 (1985).

Kuo, A. et al. "Multiple N–acyl–L–homoserine lactone autoinducers of luminescence in the marine symbiotic bacterium *Vibrio fischeri,*" *J. Bacteriol.* 176:7558–7565 (1994).

Latifi, A. M. et al. "A hierarchical quorum–sensing cascade is *P. aeruginosa* links the transcriptional activators LasR and RhlR to expression of the stationary phase sigma factor RpoS," *Mol. Microbiol.* 21:1137–1146 (1996).

Latifi, A. et al. "Multiple homologues of LuxR and LuxI control expression of virulence determinants and secondary metabolites through quorum sensing in *P. aeruginosa* PAO1," *Mol. Microbiol. Rev.* 17:333–344 (1995).

More et al. "Enzymatic synthesis of a quorum sensing autoinducer through the use of defined substrates," *Science.* 272: 1655–1658 (1996).

Ochsner, U.A. et al. "Autoinducer–mediated regulation of rhamnolipid biosurfactant synthesis in *Pseudomonas aeruginosa,*" *Proc. Natl. Acad. Sci. USA* 92:6424–6428 (1995).

Passador, L. et al. "Expression of *Pseudomonas aeruginosa* virulence genes requires cell–to–cell communication," *Science.* 260:1127–1130 (1993).

Passador, L. et al. "Functional analysis of the *Pseudomonas aeruginosa* autoinducer PAI," *J. Bateriol.* 178:5995–6000 (1996).

Pearson, J.P. et al. "Structure of the autoinducer required for expression of *Pseudonomas aeruginosa* virulence genes," *Proc. Natl. Acad. Sci. USA.* 91:197–201 (1994).

Pearson, J.P. et al. "Roles of *Pseudonomas aeruginosa* las and rhl quorum–sensing systems in control of elastase and rhamnolipid biosynthesis genes," *J. Bacteriol.* 179:5756–5757 (1997).

Pesci, E.C. et al. "The chain of command in Pseudonomas quorum sensing," *Trends in Microbiol.* 5(4); 132–135 (1997).

Pesci, E.C. et al. "Regulation of las and rhl quorum sensing systems in *Pseudonomas aeruginosa,*" *J. Bateriol.* 179:3127–3132 (1997).

Ruby, E.G. et al. "Lessons from a cooperative bacterial–animal association: the *Vibrio fischeri–Euprymna* scolopes light organ symbioses," *Ann. Rev. Microbiol.* 50:591–624 (1996).

Salmond, G.P.C. et al. "The bacterial 'engima': cracking the codes of cell–cell communication," *Mol. Microbiol.* 16:615–624 (1995).

Schaefer, A.L. et al. "Generation of cell–to–cell signals in quorum sensing: acyl homoserine lactone synthase activity of a purified *Vibrio fischeri* LuxI protein," *Proc. Natl. Acad. Sci. USA* 93:9505–9509 (1996).

Seed, P.C. et al. "Activation of the *Pseudonomas aeruginosa* lasI gene by LasR and the Pseudonomas autoinducer PAI: an autoinduction regulatory hierarchy," *J. Bacteriol.* 177:654–659 (1995).

Sitnikov, D.M. et al. "Transcriptional regulation of bioluminescence genes from *Vibrio fischeri,*" *Mol. Microbiol.* 17:801–812 (1995).

Stevens, A.M. et al. "Synergistic binding of the *Vibrio fischeri* LuxR transcriptional activator domain and RNA polymerase to the lux promoter region," *Proc. Natl. Acad. Sci. USA* 91:12619–12623 (1994).

Winson, M.K. et al. "Multiple N–acyl–L–homoserine lactone signal molecules regulate production of virulence determinants and secondary metabolites in *Pseudonomas aeruginosa,*" *Proc. Natl. Acad. Sci. USA* 92:9427–9431 (1995).

AUTOINDUCER SYNTHASE MODULATING COMPOUNDS AND USES THEREOF

RELATED APPLICATIONS

This application claims priority to the U.S. provisional patent application with Ser. No. 60/094,988 filed on Jul. 31, 1998, the entire contents of which are hereby incorporated by reference (including the originally filed claims).

BACKGROUND

Quorum sensing is cell density-dependent regulation of genes that involves a freely diffusible molecule synthesized by the cell called an autoinducer (Fuqua et al., 1996, Salmond et al., 1995, Sitnikov et al, 1995). The paradigm system for quorum sensing is the lux system of the luminescent marine bacterium, *Vibrio fischeri*. *V. fischeri* exists at low cell densities in sea water and also at very high cell densities within the light organs of various marine organisms, such as the squid *Euprymna scolopes* (Pesci et al. 1997, Ruby, 1996). At high cell densities, the *V. fischeri* genes encoding the enzymes required for light production are expressed. These genes are part of the lux ICDABEG operon and are regulated by the gene products of luxI and luxR (Baldwin et al., 1989, Eberhard et al., 1991, Gray et al. 1992). LuxI is an autoinducer synthase that catalyzes the formation of the *V. fischeri* autoinducer (VAI), N-(3oxohexanoyl) homoserine lactone (Eberhard et al. 1981, Seed et al. 1995). The autoinducer freely diffuses across the cell membrane and at high cell densities, reaches a critical concentration (Kaplan et al. 1985). At this critical concentration, VAI interacts with LuxR, a DNA-binding transcriptional regulator. The LuxR-VAI complex then binds to an upstream sequence of the lux operon called the "lux box", and activates transcription (Devine et al. 1989, Hanzelka et al. 1995, Stevens et al. 1994). Since one of the genes of the operon is luxI, an autoregulatory loop is formed.

Many gram-negative bacteria have been shown to possess one or more quorum sensing systems (Fuqua et al., 1996, Salmond et al., 1995). These systems regulate a variety of physiological processes, such as conjugal plasmid transfer in the plant pathogen *Agrobacterium tumefaciens* and antibiotic production in *Erwinia stewartii*. The systems typically have acylated homoserine lactone ring autoinducers, in which the homoserine lactone ring is conserved. The acyl side chain, however, can vary in length and degree of substitution. *Pseudomonas aeruginosa* has two quorum sensing systems, las and rhl (Brint et al. 1995, Hanzelka et al. 1996, Baldwin et al., 1989, Passador et al. 1993, Pearson et al. 1997, Pesci et al. 1997). The two systems have distinct autoinducer synthases (lasI and rhlI), transcriptional regulators (lasR and rhlR), and autoinducers (N-(3-oxododecanoyl) homoserine lactone (HSL) and N-butyryl HSL) (Sitnikov et al, 1995, Stevens et al. 1994). N-(3-oxododecanoyl) homoserine lactone is synthesized by LasI along with a small amount of N-(3-oxooctanoyl) HSL and N-(3-oxohexanoyl) HSL, while RhlI makes primarily N-butyryl HSL and a small amount of N-hexanoyl (Pearson et al. 1994, Winson et al. 1995). The rhl and las systems are involved in regulating the expression of a number of secreted virulence factors, biofilm development, and the stationary phase sigma factor (RpoS) (Brint et al. 1995, Davies et al. 1998, Latifi et al. 1996, Ochsner et al. 1995, Pesci et al. 1997). Expression of the rhl system requires a functional las system, therefore the two systems in combination with RpoS constitute a regulatory cascade (Pesci et al. 1997, Seed et al. 1995).

Quorum sensing systems are essential for communication between bacterial cells in many environments, including living biofilms. Biofilms contain distinct microcolonies, separated by discrete water channels. Biofilms are characterized by an extensive matrix of acidic polysaccharides, which protect the biofilm bacteria from biocides. In order to synthesize the polysaccharide matrix, the bacteria communicate through the quorum sensing system. Bacterial biofilms are ubiquitous and are seen in substrates ranging from sewage pipes and medical implants to teeth and the lungs of immunocompromised hosts.

SUMMARY OF THE INVENTION

The present invention is based, at least in part, on the discovery that bacterial autoinducer synthase molecules catalyze the synthesis of homoserine lactone autoinducers in a highly specific interaction of particular homoserine lactone substrates. This provided the capability to develop compositions and methods to modulate the quorum sensing capabilities of bacterial cells by controlling autoinducer production.

The present invention provides a method for identifying modulators of the autoinducer synthesis reaction, which promote or inhibit the production of homoserine lactones. Such modulators are useful for controlling bacterial growth and can be used for therapeutic treatment of bacterial infections particularly in immunocompromised subjects. They are also useful in treating disease states associated with biofilm development.

The invention pertains to methods that modulate the activity of an autoinducer synthase molecule by providing an effective amount of a compound capable of binding to the homoserine lactone substrate binding site on the autoinducer synthase molecule. The invention includes modulation of the activity of autoinducer synthase molecules including LuxI, AinS, LucM, LasI, RhlI, PhzI, TraI, HslI, EsaI, EagI, YenI, SwrI, and AhyI.

The present invention pertains to methods of selecting a compound capable of modulating the activity of the autoinducer synthase molecule by providing an effective amount of the potentially modulating compound, and determining whether the compound effectively modulates the activity of the autoinducer synthase, then selecting those compounds which do modulate the activity of the autoinducer synthase. Methods are also provided where the extent of the modulation of the activity of the autoinducer synthase is determined. A preferred embodiment pertains to a method for determining the extent of modulation by the potentially modulating compound by providing a sufficient amount of a labeled homoserine lactone substrate, allowing the reaction to go to completion, then determining the extent of the conversion of the labeled homoserine lactone substrate to homoserine lactone product.

The present invention also pertains to a method for producing highly active recombinant autoinducer synthase molecules by introducing DNA encoding the autoinducer synthase molecules into a bacterial host cell of the same species. The invention also pertains to the autoinducer synthase produced by the methods of the invention. In preferred embodiments, the purity of the autoinducer synthase is in the range from about 50–100%. In preferred embodiments, the purity of the autoinducer synthase is in the range from about 75–100%. In preferred embodiments, the purity of the autoinducer synthase is in the range from about 85–100%. In particularly preferred embodiments, the purity of the autoinducer synthase is about 95%. In a preferred embodiment, the autoinducer synthase of the RhlI quorum sensing system of *P. aeruginosa* is produced by the methods of the invention. In a particularly preferred embodiment, the RhlI autoinducer synthase has the amino acid sequence of SEQ ID NO 1. In a preferred embodiment, the RhlI autoinducer synthase has an active portion which includes amino acids 24–104. In a preferred embodiment, the RhlI autoinducer synthase has an active portion which includes amino acids 24–73. In a preferred embodiment, the RhlI autoinducer synthase has an amino acid sequence which includes Arginine 24, Glutamic Acid 46, Aspartic Acid 48 and Glutamic Acid 101.

The present invention also pertains to a method for modulating the formation of bacterial quorum system autoinducers by providing compounds which modulate the production of bacterial autoinducers by blocking the binding of homoserine lactone substrates to the homoserine lactone binding site on the autoinducer synthase molecules. In preferred embodiments, the autoinducer synthase molecules are RhlI.

The present invention also pertains to a method of modulating biofilm development in an immunocompromised individual by administering a therapeutically effective amount of an autoinducer synthase blocker. In preferred embodiments, the method is provided wherein the immunocompromised individual is afflicted with cystic fibrosis or HIV.

The present invention also pertains to a method of inhibiting the infectivity of a pathogenic bacteria by administering a therapeutically effective amount of an autoinducer synthase blocker molecule.

The invention pertains to a method of treating a subject for a disease state associated with biofilm development by administering a therapeutic composition of an autoinducer synthase blocker molecule and a pharmaceutically effective carrier. In a preferred embodiment, the invention pertains to a method of treating a human with cystic fibrosis or HIV.

The invention also pertains to a method of treating a subject for a state associated with autoinducer synthesis by administering an effective amount of an autoinducer synthase blocker.

The invention further pertains to a purified autoinducer synthase molecule. In preferred embodiments, the autoinducer synthase molecule is at least about 50% pure. In particularly preferred embodiments, the autoinducer synthase molecule is at least about 95% pure.

The invention also pertains to a biologically active autoinducer synthase molecule. In preferred embodiments, the autoinducer synthase molecule is substantially free of other contaminants. In particularly preferred embodiments, the autoinducer synthase molecule is substantially free of inclusion bodies.

The invention also pertains to a highly soluble autoinducer synthase molecule having biological activity.

DETAILED DESCRIPTION

The present invention pertains to a method for modulating the activity of an autoinducer synthase molecule by providing an effective amount of a compound capable of modulating the binding of the substrate to the homoserine lactone binding site of the autoinducer synthase molecule, such that the activity of the autoinducer synthase molecule is modulated.

The language "modulating the activity" is intended to include changes in the activity of the autoinducer synthase molecule which affect the molecule's ability to function as a catalyst or facilitate the synthesis of an autoinducer molecule. The changes include both promotion and inhibition of the activity of the autoinducer synthase molecule. The activity can be the autoinducer synthase's ability to interact with the substrate to form the autoinducer. All measurable change in activity is included. Change in activity can be measured directly by determining an increase or decrease in autoinducer synthase activity from a previously determined standard or baseline level. Alternatively, the change in activity can be measured indirectly by determining an increase or decrease in the amount of product, e.g. autoinducer, e.g. homoserine lactone autoinducer, produced or the amount of substrate consumed from a previously determined standard or baseline level.

The language "autoinducer synthase molecule" is intended to include molecules, e.g. proteins, which catalyze or facilitate the synthesis of autoinducer compounds, e.g. in the quorum sensing system of bacteria. It is also intended to include active portions of the autoinducer synthase protein contained in the protein or in fragments or portions of the protein. The language "active portions" is intended to include the portion of the autoinducer synthase protein which contains the homoserine lactone binding site. Table 1 contains a list of exemplary autoinducer synthase proteins of the quorum sensing systems of various gram-negative bacteria.

Autoinducer synthase molecules can be obtained from naturally occurring sources, e.g., by purifying cellular extracts, can be chemically synthesized or can be recombinantly produced. Recombinantly produced autoinducer synthase molecules can have the amino acid sequence of a a naturally occurring form of the autoinducer synthase protein. They can also have a similar amino acid sequence which include mutations such as substitutions and deletions (including truncation) of a naturally occurring form of the protein. Autoinducer synthase molecules can also include compounds which are structurally similar to the structures of naturally occurring autoinducer synthase proteins.

The language "purified autoinducer synthase molecule" is intended to include an autoinducer synthase molecule which has been as least partially isolated from other types of molecules with which it is typically associated in its naturally occurring environment, e.g., cellular preparations. In preferred embodiments, autoinducer synthase molecules are in preparations in which at least about 50% of the molecules are autoinducer synthase molecules. In particularly preferred embodiments, autoinducer synthase molecules are in preparations in which at least about 95% of the molecules are autoinducer synthase molecules.

The language "biologically active autoinducer synthase molecule" is intended to include an autoinducer synthase molecule which can function as a catalyst or facilitate the synthesis of an autoinducer molecule. In preferred embodiments, the autoinducer synthase molecule is substantially free of contaminants, e.g., other cellular contaminants. In particularly preferred embodiments, the autoinducer synthase molecule is substantially free of inclusion bodies.

The language "highly soluble" is art-recognized and is intended to include an autoinducer synthase molecule which is sufficiently soluble such that it functions within the methods described herein, e.g., substantially free of inclusion bodies. In preferred embodiments, the autoinducer synthase molecule is biologically active.

In a related aspect, the invention further pertains to a method for producing a highly active recombinant autoinducer synthase molecule, e.g., bacterial. This method includes introducing DNA encoding an autoinducer synthase molecule, e.g., bacterial, into a host cell of the same species, such that a highly active recombinant autoinducer synthase molecule is produced by the host cells. The molecule can be overexpressed within this method. In preferred embodiments, the host cells are grown at temperatures in the range of about 15° C.–45° C. In preferred embodiments, the host cells are grown at temperatures in the range of about 25° C.–35° C. In a particularly preferred embodiment, the cells are grown at about 30° C.

The term "highly active" is intended to include an autoinducer synthase molecule having a functional activity such that it can catalyze an interaction which produces an autoinducer product. Autoinducer synthase molecules can have functional activity in the range of a $V_{max}$ of 2.1 mol of butyryl HSL min$^{-1}$ mol$^{-1}$ of RhlI for butyryl ACP to 15.5 mol of butyryl HSL min$^{-1}$ mol$^{-1}$ of RhlI for S-adenosyl methionine. In general, such molecules are non-aggregated monomeric proteins.

The term "overexpressed" is intended to include levels of a protein produced in a recombinant host cell which are greater than those found in a non-genetically altered cell.

The language "about [X]°C." is intended to include a range of temperatures from 3° C. below the stated temperature [X]°C. to 3° C. above the stated temperature.

TraI, LuxI, RhlI are the homoserine lactone autoinducer synthases of *Agrobacterium tumefaceins*, *Vibrio fischeri*, and *Pseudomonas aeruginosa*, respectively. The term "RhlI" is intended to include proteins which catalyze the synthesis of the homoserine lactone autoinducer of the RhlI quorum sensing system of *P. aeruginosa*, butyryl homoserine lactone. The invention also pertains to the autoinducer synthase produced by the methods of the invention. In preferred embodiments, the purity of the autoinducer synthase is in the range from about 50–100%. In preferred embodiments, the purity of the autoinducer synthase is in the range from about 75–100%. In preferred embodiments, the purity of the autoinducer synthase is in the range from about 85–100%. In particularly preferred embodiments, the purity of the autoinducer synthase is about 95%.

RhlI is also intended to include active portions of the autoinducer synthase protein contained in the protein or in fragments or portions of the protein. The amino acid sequence of one RhlI protein is contained in SEQ ID NO. 1 of this application. One active portion of the RhlI protein of SEQ ID NO. 1 includes the amino acid sequence 24–104. A second active portion of the RhlI protein of SEQ ID NO. 1 includes the amino acid sequence 24–73. In addition, the particular amino acids, Arginine 24, Glutamic Acid 46, Aspartic Acid 48, and Glutamic Acid 101 have been identified as those located in highly conserved locations of RhlI.

The language "homoserine lactone substrate" is intended to include compounds which can be used as the source of the homoserine lactone moiety of the homoserine lactone autoinducer compounds, as well as optically active isomers and chemically similar analogs. The homoserine lactone moiety is shown below:

wherein R represents hydrogen in the homoserine lactone substrate and the site of attachment of the acyl moiety of the homoserine lactone autoinducer. The homoserine lactone substrate can be obtained from naturally occurring proteins, by purifying cellular extracts, or it can be chemically synthesized.

The primary homoserine lactone substrate for RhlI is S-adenosyl methionine (SAM). The structure of S-adenosyl methionine is shown below:

The homoserine lactone moiety is derived from the amino acid side chain.

The language "homoserine lactone substrate binding site" is intended to include a localized region on an autoinducer synthase molecule which interacts, e.g., binds, with a homoserine lactone substrate. This interaction catalyzes the reaction between a homoserine lactone substrate and an acylated acyl carrier protein which results in the formation of a homoserine lactone autoinducer.

The language "acylated acyl carrier protein" is intended to include both acylated acyl carrier proteins (ACPs) and other compounds which are able to supply the acyl moiety to the autoinducer such as acylated CoA. The term "acylated" is intended to refer to acyl carrier proteins with an attached acyl moiety. The attached acyl group can be butyryl, hexanoyl, octanoyl, or of the following general structure including analogs and homologs known to those skilled in the art:

wherein Y represents either hydrogen or an addition carbonyl group.

The language "autoinducer compounds" is art-recognized and is intended to include molecules, e.g., proteins which freely diffuse across cell membranes and which activate transcription of various factors which affect bacterial viability. Such compounds can affect virulence and biofilm development. Autoinducer compounds can be acylated homoserine lactones. They can be other compounds similar to those listed in Table 1. Homoserine autoinducer compounds are produced in vivo by the interaction of a homoserine lactone substrate and an acylated acyl carrier protein in a reaction catalyzed by an autoinducer synthase molecule. In isolated form, autoinducer compounds can be obtained from naturally occurring proteins by purifying cellular extracts, or they can be chemically synthesized or recombinantly produced.

TABLE 1

Summary of N-acyl homoserine lactone based regulatory systems

| Bacterial species | Signal molecules[a] | Regulatory Proteins[b] | Target function(s) |
|---|---|---|---|
| Vibrio fischeri | N-3-(oxohexanoyl)-homoserine lactone (VAI-1) | LuxI/LuxR | luxICDABEG, luxR luminescence |
| | N-(octanoyl)-L-homoserine lactone (VAI-2) | AinS/AinR[c] | luxICDABEG,? |
| Vibrio harveyi | N-β-(hydroxybutyryl)-homoserine lactone (HAI-1) | LuxM/LuxN-LuxO-LuxR[d] | luxICDABEG, luminescence and polyhydroxybutyrate synthesis |
| | HAI-2 | Lux?/LuxPQ-LuxO-LuxR[d] | luxCDABEG |
| Pseudomonas aeruginosa | N-3-(oxododecanyoyl)-L-homoserine lactone (PAI-1) | LasI/LasR | lasB, lasA, aprA, toxA, virulence factors |
| | N-(butyryl)-L-homoserine lactone (PAI-2) | RhII/RhIR | rhlAB, rhamnolipid synthesis, virulence factors |
| Pseudomonas aeureofaciens | (PRAI)[e] | PhzI/PhzR | phz, phenazine biosynthesis |
| Agroacterium tumefaciens | N-3-(oxooctanoyl)-L-homoserine lactone (AAI) | TraI/TraR-TraM | tra gens, traR, Ti plasmid conjugal transfer |
| Erwinia carotovora subsp. carotovora SCRI193 | VAI-1[f] | ExpI/ExpR | pel, pec, pep, exoenzyme synthesis |
| Erwinia carotovora subsp. carotovora SCC3193 | VAI-1[f] | CarI/CarR | cap, carbapenem antibiotic synthesis |
| Erwinia carotovora subsp. carotovora 71 | VAI-1[f] | HsII/? | pel, pec, pep, exoenzyme synthesis |
| Erwinia stewartii | VAI-1[f] | EsaI/EsaR | wts genes, exopolysaccharide synthesis, virulence factors |
| Rhizobium leguminosarum | N-(3R-hydroxy-7-cis-tetradecanoyl-L-homoserine lactone, small bacteriocin, (RLAI) | ?/RhiR | rhiABC, rhizosphere genes and stationary phase |
| Enterobacter agglomerans | VAI-1[f] | EagI/EagR | function unclear |
| Yersenia enterocolitica | VAI-1[f] | YenI/YenR | function unclear |
| Serratia liquifaciens | N-butanoyl-L-homoserine lacton (SAI-1) | SwrI/? | swarming motility |
| | N-hexanoyl-L-homoserine lacton (SAI-2) | SwrI/? | swarming motility |
| Aeromonas hydrophila | (AHAI)[e] | AhyI/AhyR | function unclear |
| Escherichia coli/?[g] | | ?/SdiA | ftsQAZ, cell division |

The present invention further pertains to a method for selecting compounds which modulate the activity of autoinducer synthases. The method includes providing an effective amount of a test compound, determining whether the activity of the autoinducer synthase molecule is modulated and selecting those compounds which modulate the activity of the autoinducer synthase molecule.

The language "autoinducer synthase modulating compounds" and "autoinducer synthase modulators" is used interchangeably herein, and is intended to include compounds which alter the interaction of the substrate to the homoserine lactone binding site on the autoinducer synthase molecule. The language "autoinducer synthase blocking compounds" is intended to include compounds which inhibit the binding of the homoserine lactone substrate to the homoserine lactone binding site on the autoinducer synthase molecules. In preferred embodiments, the autoinducer synthase blocking compounds are thio derivatives of purine nucleotides, sinefungin, and other related compounds.

Autoinducer synthase blocking compounds can also include homologs or analogs of purine nucleotides, sinefungin, and other related compounds. Autoinducer synthase blocking compounds can also include mimics. The term "mimics" is intended to include compounds which may not be structurally similar to autoinducer synthase blocking compounds but mimic the activity of autoinducer synthase blocking compounds.

The language "thio derivatives" is intended to include compounds in which sulfur has been substituted for one or more of the atoms originally contained in the compound. In preferred compounds, oxygen atoms are replaced with sulfur atoms.

The language "thio derivatives of purine nucleotides" is intended to include compounds formed by at least one substitution of sulfur for oxygen in purine nucleotides, preferably at the 5' position of the ribose sugar ring. It also includes any chemically equivalent compounds, such as those resulting from substitutions, deletions, or additions anywhere on the nucleotide, such as thio substitutions at other places on the ribose ring or nucleic acid.

The language "alkylated thio derivatives of purine nucleotides" is intended to include "thio derivatives of purine nucleotides" which have an aliphatic group bonded directly to the sulfur which is also bound to the purine nucleotide. The aliphatic group can be straight or branched, typically having between 1 and 22 carbon atoms. Aliphatic groups include alkyl groups, alkenyl groups and alkynyl groups. In complex structures, the chains can be branched or cross-linked. Alkyl groups include saturated hydrocarbons having one or more carbon atoms, including straight-chain alkyl groups and branched-chain alkyl groups. Such hydrocarbon moieties may be substituted on one or more carbons with, for example, a halogen, a hydroxyl, a thiol, an amino, an alkoxy, an alkylcarboxy, an alkylthio, or a nitro group. Unless the number of carbons is otherwise specified, "lower aliphatic" as used herein means an aliphatic group, as defined above (e.g., lower alkyl, lower alkenyl, lower alkynyl), but having from one to six carbon atoms. Representative of such lower aliphatic groups, e.g., lower alkyl groups, are methyl, ethyl, n-propyl, isopropyl, 2-chloropropyl, n-butyl, sec-butyl, 2-aminobutyl, isobutyl, tert-butyl, 3-thiopentyl, and the like. As used herein, the term "amino" means —$NH_2$; the term "nitro" means —$NO_2$; the term "halogen" designates —F, —Cl, —Br or —I; the term "thiol" means $SH_2$; and the term "hydroxyl" means —OH. Thus, the term "alkylamino" as used herein means an alkyl group, as defined above, having an amino group attached thereto. The term "alkylthio" refers to an alkyl group, as defined above, having a sulphydryl group attached thereto. The term "alkylcarboxyl" as used herein means an alkyl group, as defined above, having a carboxyl group attached thereto. The term "alkoxy" as used herein means an alkyl group, as defined above, having an oxygen atom, attached thereto. Representative alkoxy groups include methoxy, ethoxy, propoxy, tert-butoxy and the like. The terms "alkenyl" and "alkynyl" refer to unsaturated aliphatic groups analogous to alkyls, but which contain at least one double or triple bond respectively. The term "alkylated thio derivatives of purine nucleotides" is also intended to include any homologs or analogs, which have similar autoinducer synthase blocking activity. Preferred embodiments include 5'-methylthioadenosine, S-adenosyl homocysteine, and S-adenosyl cysteine The language "test compound" is intended to include compounds which potentially modulate the activity of an autoinducer synthase molecule. Test compounds may be purchased, chemically synthesized or recombinantly produced. Test compounds can be obtained from a library of diverse compounds based on a desired activity, or alternatively they can be selected from a random screening procedure. Preferably, the test compounds of the present invention are molecules having a moiety which binds to the homoserine binding site of the autoinducer synthase molecule. In preferred embodiments the moiety is a purine nucleotide moiety. The term "moiety" is intended to include synthetic and naturally-occurring entities.

The term "labeled" is intended to include compounds which are readily identifiable by, for example, radioactive labels (H3, C14, O18, etc.) or fluorescence.

The language "an effective amount of a compound" is intended to include the amount necessary or sufficient to produce a modulating effect in the activity of the condition being treated. In the case of an autoinducer synthase modulating compound, an effective amount is the amount necessary to sufficiently promote or inhibit the activity of the autoinducer synthase molecule such that the amount of autoinducer produced is either decreased or increased.

The invention pertains to a method for modulating the formation of bacterial quorum sensing system autoinducers by providing an effective amount of a compound capable of modulating the binding of a substrate to the homoserine lactone substrate binding site of the autoinducer synthase, such that the formation of bacterial quorum sensing system autoinducers is modulated.

The language "bacterial quorum sensing system" is intended to include the cell-to cell communication system of gram-negative bacteria which enables population density control of gene expression.

The language "gram-negative bacteria" is intended to include those bacteria which stain pink when treated with Gram's Stain.

The invention pertains to a method for modulating bacterial biofilm development by providing an effective amount of a compound capable of modulating the binding of a substrate to the homoserine lactone substrate binding site of an autoinducer synthase, such that the development of the bacterial biofilm is modulated. The term "biofilm" is intended to include biological films that develop and persist at interfaces in aqueous environments. Biofilms are composed of microorganisms embedded in an organic gelatinous structure composed of one or more matrix polymers which are secreted by the resident microorganisms.

The language "biofilm development" is intended to include the formation growth, and modification of the bacterial colonies contained with the biofilm structures as well as the synthesis and maintenance of the exopolysaccharide matrix of the biofilm structures.

The invention pertains to a method of inhibiting the infectivity of a pathogenic bacteria in a subject comprising administering a therapeutically effective amount of an autoinducer synthase blocker, such that the infectivity of a pathogenic bacteria is inhibited.

The language "inhibiting the infectivity" is intended to include any mitigation of the ability of a pathogenic bacteria to either initiate a disease state within a subject or to sustain a disease state within a subject.

The language "pathogenic bacteria" is intended to include any bacteria capable of initiating a disease state within a subject or sustaining a disease state within a subject. Examples of such bacteria include gram-negative bacteria, e.g. *P. aeruginosa*.

The invention also pertains to a method of treating a subject for a state associated with autoinducer synthesis by administering an effective amount of an autoinducer synthase blocker, such that treatment occurs.

The language "state associated with autoinducer synthesis" is intended to include states or conditions in which autoinducer synthesis causes or increases symptoms which can be detrimental to a subject. Examples of such states include those associated with biofilm development, e.g., bacterial infections.

The invention also pertains to a method of treating an immunocompromised subject by administering a therapeutically effective amount of an autoinducer synthase blocking compound to the subject such that treatment occurs.

The language "immunocompromised subject" is art-recognized and is intended to include subjects having an immune system which is compromised, at least in part. For example, the subject can be immunocompromised due to a genetic disorder, disease or drugs that inhibit the immune response. The compromise of the immune system can be temporary or permanent. An immunocompromised subject includes individuals who are afflicted with HIV or cystic fibrosis, or who are taking corticosteroids or immunosuppressive agents.

The phrase "therapeutically-effective amount" as used herein means an amount of a autoinducer synthase modulator, or composition comprising such a compound which is effective for the autoinducer synthase modulator to produce its intended function, e.g., the modulation of the synthesis of autoinducers. The effective amount can vary depending on such factors as the type of activity being modulated, the particular type of autoinducer synthase molecule, the size of the subject, or the severity of the state being treated or the activity. One of ordinary skill in the art would be able to study the aforementioned factors and make the determination regarding the effective amount of the autoinducer synthase modulator without undue experimentation.

The terms "subject" or "subjects" as used herein, means a living animal, susceptible to the conditions or state described herein. Examples include reptiles, rodents, horses, sheep, cattle, dogs, cats, gorillas, and humans. It also includes healthy animals and those suffering from diseases characterized by the infection of pathogenic bacteria.

The invention pertains to methods of treating a subject for a disease state associated with biofilm development by administering a therapeutically effective amount of an autoinducer synthase blocking compound, such that biofilm development is inhibited.

The language "disease state associated with biofilm development" is intended to include diseases characterized by the growth of bacterial biofilms. In preferred embodiments the disease state is a bacterial infection.

The phrase "pharmaceutically acceptable" is employed herein to refer to those autoinducer synthase modulators, compositions containing such compounds, and/or dosage forms which are, within the scope of sound medical judgment, suitable for use in treating human beings and animals without excessive toxicity, irritation, allergic response, or other problem or complication, commensurate with a reasonable benefit/risk ratio.

Autoinducer synthase modulators of the present invention can exist in free form or, where appropriate, in salt form. Pharmaceutically acceptable salts and their preparation are well-known to those of skill in the art. The pharmaceutically acceptable salts of such compounds include the conventional non-toxic salts or the quaternary ammonium salts of such compounds which are formed, for example, from inorganic or organic acids of bases.

The compounds of the invention may form hydrates or solvates. It is known to those of skill in the art that charged compounds form hydrated species when lyophilized with water, or form solvated species when concentrated in a solution with an appropriate organic solvent.

This invention also relates to pharmaceutical compositions comprising a therapeutically (or prophylactically) effective amount of the autoinducer synthase modulator, and a pharmaceutically acceptable carrier or excipient. Carriers include e.g. saline, buffered saline, dextrose, water, glycerol, ethanol, and combinations thereof, and are discussed in greater detail below. The composition, if desired, can also contain minor amounts of wetting or emulsifying agents, or pH buffering agents. The autoinducer synthase modulator can be a liquid solution, suspension, emulsion, tablet, pill, capsule, sustained release formulation, or powder. The autoinducer synthase modulator can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Formulation may involve mixing, granulating and compressing or dissolving the ingredients as appropriate to the desired preparation.

The pharmaceutical carrier employed may be, for example, either a solid or liquid.

Illustrative solid carrier include lactose, terra alba, sucrose, talc, gelatin, agar, pectin, acacia, magnesium stearate, stearic acid and the like. A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions, and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Illustrative liquid carriers include syrup, peanut oil, olive oil, water, etc. Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl imyristate. Sterile liquid carders are useful in sterile liquid form compositions for parenteral administration. The liquid carrier for pressurized compositions can be halogenated hydrocarbon or other pharmaceutically acceptable propellant. Liquid pharmaceutical compositions which are sterile solutions or suspensions can be utilized by, for example, intramuscular, intraperitoneal or subcutaneous injection. Sterile solutions can also be administered intravenously. The autoinducer synthase modulator can also be administered orally either in liquid or solid composition form.

The carrier or excipient may include time delay material well known to the art, such as glyceryl monostearate or glyceryl distearate along or with a wax, ethylcellulose, hydroxypropylmethylcellulose, methylmethacrylate and the like.

A wide variety of pharmaceutical forms can be employed. If a solid carrier is used, the preparation can be tableted, placed in a hard gelatin capsule in powder or pellet form or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable solution or suspension in an ampule or vial or nonaqueous liquid suspension.

To obtain a stable water soluble dosage form, a pharmaceutically acceptable salt of a autoinducer synthase modulator may be dissolved in an aqueous solution of an organic or inorganic acid, such as a 0.3 M solution of succinic acid or citric acid. Alternatively, acidic derivatives can be dissolved in suitable basic solutions. If a soluble salt form is not available, the compound is dissolved in a suitable cosolvent or combinations thereof. Examples of such suitable cosolvents include, but are not limited to, alcohol, propylene glycol, polyethylene glycol 300, polysorbate 80, glycerin, polyoxyethylated fatty acids, fatty alcohols or glycerin hydroxy fatty acids esters and the like in concentrations ranging from 0–60% of the total volume.

Various delivery systems are known and can be used to administer the autoinducer synthase modulator, or the various formulations thereof, including tablets, capsules, injectable solutions, encapsulation in liposomes, microparticles, microcapsules, etc. Methods of introduction include but are not limited to dermal, intradermal, intramuscular, intraperitoneal, intravenous, subcutaneous, intranasal, pulmonary, epidural, ocular and (as is usually preferred) oral routes. The compound may be administered by any convenient or otherwise appropriate route, for example by infusion or bolus injection, by absorption through epithelial or mucocutaneous linings (e.g., oral mucosa, rectal and intestinal mucosa, etc.) and may be administered together with other biologically active agents. Administration can be systemic or local. For treatment or prophylaxis of nasal, bronchial or pulmonary conditions, preferred routes of administration are oral, nasal or via a bronchial aerosol or nebulizer.

In certain embodiments, it may be desirable to administer the autoinducer synthase modulator locally to an area in need of treatment; this may be achieved by, for example, and not by way of limitation, local infusion during surgery, topical application, by injection, by means of a catheter, by means of a suppository, or by means of a skin patch or implant, said implant being of a porous, non-porous, or gelatinous material, including membranes, such as sialastic membranes, or fibers.

In a specific embodiment, the autoinducer synthase modulator is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Administration to an individual of an effective amount of the compound can also be accomplished topically by administering the compound(s) directly to the affected area of the skin of the individual. For this purpose, the compound is administered or applied in a composition including a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils.

Other topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary. Percutaneous penetration enhancers such as Azone may also be included.

In addition, in certain instances, it is expected that the compound may be disposed within devices placed upon, in, or under the skin. Such devices include patches, implants, and injections which release the compound into the skin, by either passive or active release mechanisms.

Materials and methods for producing the various formulations are known in the art and may be adapted for practicing the subject invention.

The amount of compound which will be effective in the treatment or prevention of a particular disorder or condition will depend in part on the nature of the disorder or condition, and can be determined by standard clinical techniques. In addition, in vitro or in vivo assays may optionally be employed to help identify optimal dosage ranges. Effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies; and the nature and extent of genetic engineering of cells in the patient.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically", "peripheral administration" and "administered peripherally" as used herein mean the administration of a autoinducer synthase modulator, drug or other material, such that it enters the subject's system and, thus, is subject to metabolism and other like processes, for example, subcutaneous administration.

The invention also provides a pharmaceutical package or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceutical or biological products, which notice reflects approval by the agency of manufacture, use or sale for human administration. The package also can include instructions for using the autoinducer synthase modulator within the methods of the invention.

This invention is further illustrated by the following examples which in no way should be construed as being further limiting. The contents of all references, pending patent applications and published patent applications, cited throughout this application (including the background section) are hereby incorporated by reference.

EXAMPLES

Materials and Methods

Bacterial Strains, Plasmids and Growth Conditions

All cloning and basic genetic manipulations were performed in *E. coli* XL1-Blue. All molecular biology enzymes were purchased from New England Biolabs (Beverly, Mass.). The RhlI overexpression vector, pRhlI-2, was constructed by cloning an 899 bp BamH I-Hind III fragment (containing the rhlI gene under control of the tac promoter and the lacUV5 Shine Dalgarno) from pRhlI-1 into BamH I-Hind III-digested pBBR1MCS5 (Gm'). This plasmid, pBBR1MCS5, is a broad host range vector containing the multicloning site from pBluescript II SK+. The plasmid pRhlI-2 was then electroporated into *P. aeruginosa* PAO-JP1 (PAO1 derivative; transposon insertion in lasit Tet') and selected for PTSB agar plates supplemented with Gm (25 µg/ml) and Tet (50 µg/ml). The plasmid pRhlI-1A was constructed by cloning an EcoR I-Hind III-digested 647 bp PCR product containing the rhlI gene fused to the T7 gene 10 rbs into EcoR I-Hind III-digested pEX1.8 (Broad host range derivative of pKK223-3, Cb'). This has an improved Shine Dalgarno sequence and seven bases between the Shine Dalgarno and the translational start site instead of the suboptimal 10 bases of pKK223-3. The plasmid pECP61.5 was used in *E. coli* XL1-Blue for the butyryl homoserine lactone (HSL) bioassay.

Electroporation was performed as follows a 500 µl inoculation of an overnight culture of PAO-JP1 was added to a fresh culture of PTSB supplemented with Tet (50 µg/ml). The culture was grown at 37° C. for about 5 hr to an $OD_{600}$ of approximately 0.45. This culture was spun down at 5000×g for 5 min and resuspended in ½ volume of ice-cold 300 mM sucrose. The cells were pelleted at 4° C. and resuspended in 1/50 volume of 300 mM sucrose. About 500 ng of plasmid DNA was added to 100 µl of cells and allowed to sit on ice for about 5 min. The cells were then electroporated (2.5 V, 25 µFd, 200 Ω), 700 µl of fresh PTSB was added and the cells were allowed to incubate at 37° C. for 1 hr. The cells were then plated out on selective media.

Purification of RhlI

Conditions were optimized for RhlI expression in PAO-JP1. Crude cell lysates of cells grown under different conditions were generated using sonication and run on a 12% SDS polyacrylamide gel (SDS-PAGE). Protein concentrations were determined using Bradford assays (Bio Rad, Hercules, Calif.). The gels were blotted onto nitrocellulose and western analysis was conducted using RhlI antisera. RhlI expression was found to be maximal in cells grown at 30° C. and harvested at an $OD_{600}$ of 0.850.

Ten liters of a PAO-JP1/pRhlI-2 was grown to an $OD_{600}$ of 0.850 on PTSB broth in a 10 L Biostat B fermentor (B Braun Biotec, Inc., St. Louis, Mo.). The cells were harvested by centrifugation at 4° C. for 10 min at 5,000×g. The cells were washed once in ice cold purification buffer I (20 mM KPO ph=7.5, 10% glycerol, 0.1 mM DL-Dithiothretol (DTT), 0.1 mM EDTA, 1 mM Phenylmethylsulfonyl fluoride (PMSF) and then centrifuged again. The cell pellet was resuspended in 70 ml of purification buffer I and subjected to lysis in a french pressure cell. Two passes were made over the french pressure cell at 8,000 psi and the sample was centrifuged at 12,000×g for 30 min at 4° C. The soluble fraction was centrifuged again at 74,000×g for 60 min. The crude extract was loaded onto a 5 ml HITRAP Q (Pharmacia, Piscataway, N.J.) column equilibrated in purification buffer I. The column was then washed and then subjected to a 75 ml 0–1 M NaCl gradient in purification buffer I. The flow rate was 2 ml/min and 25, 3-ml fractions were collected. The protein from each fraction was run on an SDS-PAGE polyacrylamide gel and the fraction containing RhlI were detected by western analysis. Fractions containing RhlI were pooled and buffer exchanged with 0 M NaCl purification buffer II (same as buffer I, except pH=5.8) using a Centriplus 10 spin column (Amicon, Beverly, Mass.). The pooled fractions were loaded onto a HITRAP S (Pharmacia, Piscataway, N.J.) column and the column was then washed in 0 M NaCl purification buffer II. A 75 ml 0–1 M NaCl gradient was run at a flow rate of 2 ml/min and 25 fractions were collected. The fractions were subjected to SDS-PAGE and western analysis. The RhlI-containing fractions were pooled, buffer exchanged in purification buffer III (same as buffer I, except pH=7.2) and concentrated down to 4 ml volume. Two 2-ml fractions were loaded onto a 100 ml Superdex 75 column (Pharmacia, Piscataway, N.J.) and run at a flow rate of 0.4 ml/min in purification buffer III. RhlI eluted in two 5-ml fractions. The RhlI containing fractions were pooled, run on an SDS-PAGE gel, and stained with Coomassie blue and estimated to be about 95% pure.

Determination of RhlI Substrates Using Bioassays

Purified RhlI was assayed for activity in vitro. Reactions were conducted using purified RhlI (72 ng) in a 100 µl reaction containing 1× reaction buffer (20 mM Tris-Cl pH=7.8, 2 mM DTT, 200 mM NaCl), 114 µM SAM, and 40 µM butyryl-ACP. The reaction was allowed to proceed for 30 min at 37° C. The reaction was terminated by the addition of 4 µl of 1 M HCl. The reaction was then extracted twice with equal volumes of acetified ethyl acetate. The organic phase was collected and dried down in a 13 mm culture tube with N2 gas. The material was resuspended in 500 µl of A media and subjected to the RhlI bioassay as previously described. Other substrates were tested in the assay by replacing either SAM or butyryl-ACP. The compounds tested as possible substrates were: butyryl-CoA (565 µM), hexanoyl-ACP (43.8 µM), octanoyl-ACP (44 µM), butyrate (1 mM), S-adenosyl homocysteine (650 µM), S-adenosyl cysteine (400 µM), homoserine lactone (400 µM), homocysteine (400 µM), homoserine (400 µM), and methionine (400 µM).

Radioactive Assay for in vitro RhlI Activity

To facilitate kinetic analysis of RhlI in vitro, an assay was developed using C14-labeled SAM (Amersham, Arlington Heights, Ill.). The labeled carbon is in the carboxyl group, and is thus incorporated into the autoinducer product. When an aqueous solution is extracted with acetified ethyl acetate, SAM remains in the aqueous phase. However, acyl HSLs will partition into the organic phase of an ethyl acetate extraction. After two extractions with equal volumes of ethyl acetate, approximately 99% of the acyl HSL is in the organic phase. The assay was performed in 1.5 ml siliconized eppendorf tubes. The 100 µl reactions contained: 1× reaction buffer buffer (20 mM Tris-Cl pH=7.8, 2 mM DTT, 200 mM NaCl), purified RhlI, and desired concentrations of acyl-ACP and unlabeled SAM supplemented with radioactive SAM. The concentration of radioactive SAM used regardless of the concentration of unlabeled SAM was 4 µM (1 µl of 60 µCi/µmole stock solution). Reactions were initiated by adding 72 ng of RhlI, allowed to proceed for 10 min at 37° C. and then terminated by addition of 4 µl of 1 M HCl. The reactions were extracted twice with equal volumes of acetified ethyl acetate and centrifuged after each extraction for 5 min in a microcentrifuge at 10,000×g. The ethyl acetate phase was then added to 4 ml of Budget-solve (Research Products International, Mount Prospect, Ill.) scintillation cocktail and then counted for 1 min on a Beckman LS1800 scintillation counter (Beckman Instruments, Inc., Palo Alto, Calif.). The calculated total acyl HSL produced in the reaction accounted for the ratio of unlabeled to labeled SAM. This assay was used to monitor the activity of RhlI during the different steps throughout the purification process and to determine the kinetic characteristics of RhlI.

High Pressure Liquid Chromatography (HPLC) analysis of reaction products were conducted by drying down ethyl acetate extracts of in vitro reactions and solubilizing them in 250 μl of 20% methanol in water. The sample was then applied to a Nucleosil C18 reverse phase 5 μM HPLC column (Sigma, Inc., St. Louis, Mo.) and a 20–100% methanol gradient was applied and fractions collected as described previously. The 2-ml fractions were collected in scintillation vials, 4 ml of Budget-solve were added, and the fractions were counted in a scintillation counter. Characteristic retention times of acyl HSLs were used to verify radio-labeled reaction products. HPLC analysis was used to resolve products of reactions containing both butyryl-ACP and hexanoyl-ACP substrates.

Analysis of Kinetic Parameters of RhlI

To determine the kinetic constants of acyl HSL synthesis by RhlI, radioactive in vitro assays were conducted using its different substrates. The kinetic constants for the different substrates were determined by plotting out initial velocity data using Lineweaver-Burk plots. To generate the Lineweaver Burk plots, Cleland's kinetics programs were used (G.X.H. and B.V.P., University of Iowa, © 1993). To determine the apparent $K_m$ of RhlI for SAM, a range of concentrations were used for SAM (4–95 μM) with butyryl-ACP remaining fixed at 58 μM. The $K_m$ of butyryl-ACP was determined by holding the SAM concentration at 95 μM and varying the butyryl-ACP (3.9–58 μM). The amount of RhlI used in these reactions was 72 ng. The $K_m$'s for hexanoyl ACP and octanoyl-ACP were determined by holding the SAM concentration at 95 μM and varying the hexanoyl-ACP concentration (8.65–692 μM) and the octanoyl-ACP concentration (4.4–264 μM). The amount of RhlI added for these in vitro reactions were 144 ng and 1.44 μg for hexanoyl-ACP and octanoyl-ACP containing reactions, respectively. Butyryl-CoA concentrations were varied (28–798 μM) and 3.6 μg of RhlI was used to determine the $K_m$ of RhlI for butyryl-CoA.

Example 1

Overexpression and Purification of an Autoinducer Synthase

Initially studies were conducted at temperatures ranging from 20° to 37° C. to determine the optimal RhlI overexpression conditions. Two RhlI overexpression plasmids were tested for production of soluble RhlI. The plasmid pRhlI-2 was a broad host range vector that has RhlI fused to the suboptimal Shine Dalgarno of pKK223-3, whereas pRhlI-1A had the RhlI gene fused to a the T7 early gene 10 Shine Dalgarno with optimal spacing. Initial experiments in E. coli determined that although RhlI was expressed at high levels from pRhlI-1A, almost all the RhlI produced was insoluble. The RhlI expressed from pRhlI-2 was at as high of levels as in pRhlI-1A, however only a small amount remained insoluble (<10%) as determined by western analysis. Although expression in P. aeruginosa was not as high as in E. coli, the solubility was much improved. The greatest amount of soluble RhlI (90% of total produced in cells) generated was in PAO-JP1/pRhlI-2 cells grown at 30° C. At higher temperatures, RhlI was expressed at higher level but it occurred as insoluble aggregates. This suggested that P. aeruginosa ability to produce properly folded, soluble protein, was sensitive to the levels of RhlI produced.

The purification process was monitored using SDS-PAGE and western analysis, as well as using the in vitro radioactive assay (see Material and Methods). The RhlI purification process yielded pure (estimated to be ~95% pure by SDS-PAGE), soluble, active protein (see Table 2 below). Purified RhlI migrated in SDS-PAGE gels at approximately 26 kDa, which is slightly larger than the predicted value (~22 kDa). Similar observations have been reported for other LuxI family members. RhlI eluted at about 25 kDa on a superdex 75 size exclusion column, which would approximately correspond to a monomer of RhlI in solution.

The overexpression of RhlI in a PAO-JP1 background yielded 3.6 mg of pure protein from 10 L of culture. Visual inspection of SDS-PAGE gels shows significant increases in the RhlI band intensity relative to contaminants in every purification step. However, the specific activity of the different pooled fractions following each step gradually increases until the final step where it increases markedly (see Table 2 below). The calculated total number of units increases from 1,649 in the S sepharose fraction to 7,430 in the S-75 fraction. Glycerol was added to the purified RhlI preparation at a final concentration of 20%. The protein was then aliquotted and stored at −70° C. This protein was used in subsequent in vitro reactions.

TABLE 2

Purification of RhlI

| purification step | total activity (units)[a] | total protein (mg) | purification (x-fold) | specific activity (units/mg) | recovery % |
|---|---|---|---|---|---|
| crude extract | 18,228 | 840 | 1 | 21.7 | 100 |
| Q sepharose | 10,899 | 315 | 1.59 | 34.6 | 59.7 |
| S sepharose | 1,649 | 26.6 | 2.85 | 62 | 9.0 |
| S 75 size exclusion | 7,430 | 3.6 | 95.1 | 2,064 | 40.7 |

[a]one unit is defined as nanomoles of product formed per minute.

Example 2

Examination of Autoinducer Synthase Substrates Using in vitro Reactions Coupled with Bioassays An initial screen for RhlI substrates was conducted by extracting in vitro reactions with ethyl acetate and assaying dried down extracts in the butyryl HSL bioassay. The amount of acyl HSL synthesized was quantified by comparing activity in the rhl bioassay to standard curves generated using either synthetic butyryl HSL or hexanoyl HSL. The reacting using octanoyl-ACP was tested in the Ralstonia solanacerarum bioassay, which is sensitive to octanoyl HSL. The potential RhlI substrates that were tested are listed in Table 3. The in vitro synthesis of acyl HSLs was completely dependent upon RhlI. Likewise, acyl HSL synthesis did not occur in the absence of one or both of the substrates. No compound other than SAM served as a substrate for RhlI and as a source of the homoserine lactone ring moiety of butyryl HSL. A very small amount of activity was detected in the reactions containing homocysteine. This activity is at least 150-fold less when compared to reactions containing SAM (see Table 3 below).

There was a great deal of flexibility in the substrates that can be used only by RhlI as a source of the acyl group. Both butyryl-CoA and butyryl-ACP can serve as a substrate for butyryl HSL synthesis, although butyryl-ACP appears to be the preferred substrate. Butyrate did not have activity in vitro. Presumably the acyl group has to be bound via a thioester linkage to the phosphopantetheine moiety of either CoA or ACP. Hexanoyl-ACP is a substrate for the synthesis of hexanoyl HSL by RhlI.

TABLE 3

Compounds tested as potential RhlI substrates

| Compound[a] | Activity in butyryl HSL bioassay[b] | Activity in radioactive assay[b] |
|---|---|---|
| butyryl-ACP | 532 | 650 |
| butyryl-ACP + NADPH | ND | 718 |
| butyryl-CoA | 38 | 82 |
| butyrate | — | — |
| B-OH butyryl-CoA | ND | — |
| hexanoyl-ACP | 91 | 263 |
| hexanoyl-CoA | — | 4 |
| octanoyl-ACP | —[c] | 28 |
| octanoyl-CoA | ND | — |
| decanoyl-CoA | ND | — |
| S-adenosyl homocysteine | — | ND |
| S-adenosyl cysteine | — | ND |
| homoserine lactone | — | ND |
| homocysteine | <2 | ND |
| homoserine | — | ND |
| methionine | — | ND |

ND Not determined
[a]61 μM SAM was used as a substrate in reactions testing potential acyl group substrates.
39 μM butyryl ACP was used in reactions testing potential amino acid substrates.
[b]the units of activity for the butyryl HSL bioassay and the radioactive assay are nmoles butyryl HSL formed $min^{-1}$ $mg^{-1}$.
[c]This reaction was tested in the *R. solanacearum* bioassay

Example 3

Radioactive in vitro Assay for Activity of an Autoinducer Synthase

Figure 1A:
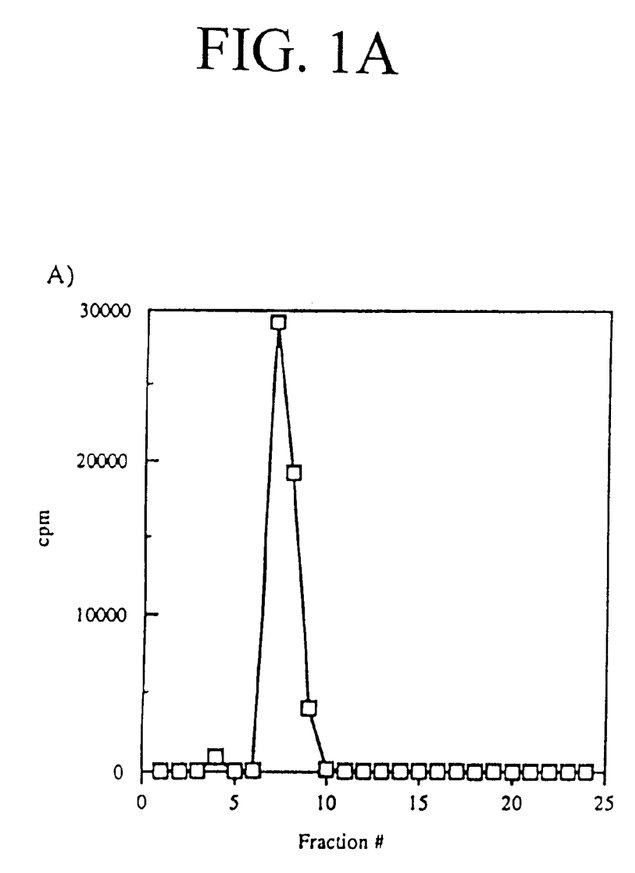
FIG. 1A is a representation of an high performance liquid chromotography analysis demonstrating that butyryl homoserine lactone is produced from S-adenosylmethionine.

To facilitate the study of acyl HSL synthesis by RhlI, an in vitro assay using $C^{14}$-labeled SAM was developed. This assay was initially used to monitor the synthesis of butyryl HSL using the substrates SAM (65 μM) and butyryl-ACP (39 μM). The reaction products were subjected to HPLC analysis to verify that the radioactive component in the extracted ethyl acetate phase corresponded to butyryl HSL. The major radioactive product co-eluted with unlabeled butyryl HSL (FIG. 1A). This result verified that RhlI is an autoinducer synthase requiring only butyryl-ACP and SAM as substrates. A small peak of activity eluted in the void volume of the column (FIG. 1A). Similar reactions performed with hexanoyl-ACP or octanoyl-ACP produced peaks that correspond to the retention times of cold hexanoyl-ACP or octanoyl HSL, respectively. These reactions also had a very small peak of activity in fraction #4. This peak is responsible for the small amount of radioactivity present in the negative controls for the radioactive in vitro reactions and was subtracted out of the total counts for reactions. A reaction using butyryl-CoA as a substrate and analyzed with HPLC demonstrated there was a single peak of radioactivity corresponding to butyryl HSL. There was no detectable hexanoyl HSL peak indicative of contamination of the Sigma butyryl-CoA with hexanoyl-CoA as reported previously in other studies.

Figure 1B:
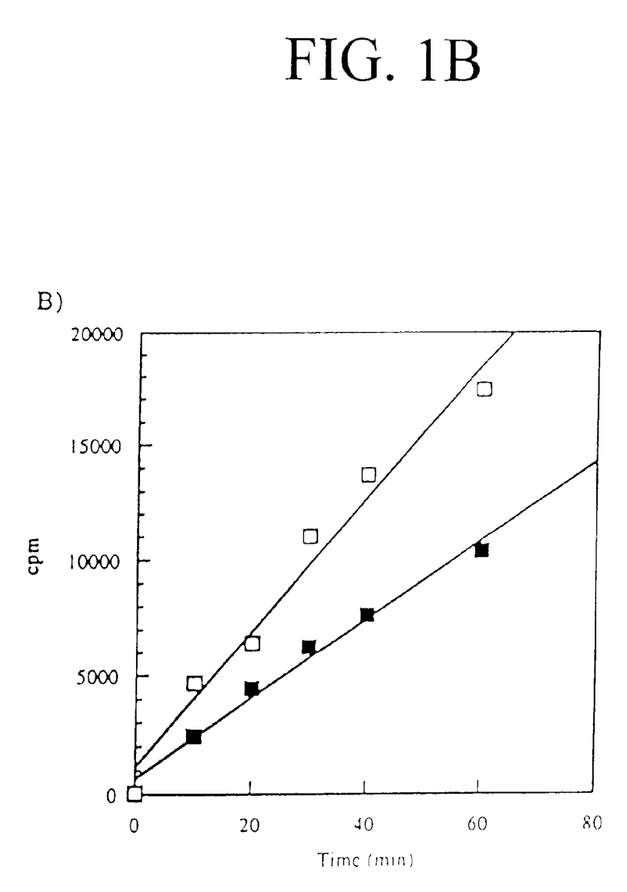
FIG. 1B is a graphic representation of the performance criteria of an assay which measures autoinducer synthase activity.

This assay was shown to satisfy the basic criteria of standard enzymatic assays. The reaction was linear over time and dependent upon the concentration of the enzyme (see FIG. 1B). The reactions remained linear for up to 90 min. using the enzyme concentrations tested. The synthesis of hexanoyl HSL and octanoyl HSL in this assay was also shown to be linear over time and dependent upon the concentration of the enzyme. No product was detectable if RhlI or either of the two substrates were omitted (SAM or any of the acyl-CoAs or acyl-ACPs). This assay is dependent upon radioactive SAM, therefore it is limited to testing different acyl chain substrates.

The activities of different acylated compounds of substrates were tested in the radioactive assay (Table 3). The most active acyl substrates were butyryl-ACP and hexanoyl-ACP, similar to the bioassay results. This analysis proved to be more sensitive than the coupled in vitro reactions and bioassays. Octanoyl-ACP was demonstrated to be a substrate of RhlI. It was not detected as a substrate in the coupled in vitro reaction-bioassays. NADPH, included with butyryl-ACP and SAM, was found to slightly increase the reaction rate.

Example 4

Kinetic Parameters of an Autoinducer Synthase Mediated Autoinducer Synthesis To determine the kinetic parameters of RhlI, in vitro radioactive assays were performed. A wide range of concentrations for the tested compounds were assayed at a high, fixed concentration of the other substrate. These initial velocity studies were conducted at time points where the pseudo-first order reactions was proceeding at a linear rate. The data was fitted to Lineweaver-Burke plots and the kinetic constants were determined for the following substrates: SAM, butyryl-ACP, butyryl-CoA, hexanoyl-ACP, and octanoyl-ACP (Table 4). The $K_m$ of RhlI for SAM was 14 μM. For acyl substrates, RhlI had the lowest $K_m$ for butyryl-ACP (6 μM), although the $K_m$ for hexanoyl-ACP is comparable (8 μM). The $K_m$'s for octanoyl-ACP and butyryl-CoA were 43 μM and 230 μM, respectively. The maximum velocities of the reactions ($V_{max}$) with butyryl-ACP and hexanoyl-ACP are comparable, whereas the velocities of the reactions containing octanoyl-ACP and butyryl-CoA are at least 5-fold lower. Reactions conducted with saturating levels (40 μM) of both butyryl-ACP and hexanoyl-ACP showed that butyryl-APC is the preferred substrate, with butyryl HSL and hexanoyl HSL produced at a ratio of 20:1.

TABLE 4

Kinetic parameters for different substrates

| Substrate | Apparent $K_m$[a] | Apparent $V_{max}$[b] |
|---|---|---|
| S-adenosyl methionine | 14 | 15.5 |
| butyryl ACP | 6 | 15.5 |
| butyryl CoA | 230 | 2.1 |
| hexanoyl ACP | 8 | 9.6 |
| octanoyl ACP | 43 | 1.8 |

[a]The unit of measurement is μM.
[b]The units of measurement are mol of butyryl HSL $min^{-1}$ $mol^{-1}$ of RhlI.

REFERENCES

1. Baldwin, T. O., J. H. Devine, R. C. Heckel, J. W. Lin, and G. S. Shadel. 1989. The complete nucleotide sequence of the lux regulon of *Vibrio fischeri* and the luxABN region of *Photobacterium leignathi* and the mechanism of control of bacterial bioluminescence. J. of Biolum. and Chemilum. 4:326–341.
2. Bassler, B. L., M. Writght, R. E. Showalter, and M. R. Silverman. 1993. Intracellular signaling in *Vibrio harveyi*: sequence and function of genes regulating expression of luminescence. Mol. Microbiol. 9:773–786.

3. Brint, J. M. and D. E. Ohman. 1995. Synthesis of multiple exoproducts in *P. aeruginosa* is under control of RhlR-RhlI another set of regulators in strain POAI with homology to the autoinducer responsive LuxR-LuxI family. J Bacteriol. 177: 7155–7163.
4. Davies, D. G., M. R. Parsek, J. P. Pearson, B. H. Iglewski, J. W. Costerton and E. P. Greenberg. 1998. The involvement of cell-to-cell signals in the development of a bacterial biofilm. Science. 280: 295–298.
5. Devine, J. H. G. S. Shadel, T. O. Baldwin. 1989. Identification of the operator of the lux regulon from *Vibrio fisheri* strain ATCC 7744. Proc. Natl. Acad. Sci. USA 86: 5688–5692.
6. Eberhard, A., A. L. Burlingame, C. Eberhard, G. L. Kenyon, K. H. Nealson and N. J. Opperheimer, 1981. Structural identification of autoinducer of *Photobacterium fisceri* luciferase. Biochemistry. 20:2444–2449
7. Eberhard, A., T. Longin, C. A. Widrig, and S. J. Stanick, 1991. Synthesis of the lux gene autoinducer in *Vibrio fischeri* is positively autoregulated. Arch. of Microbiol. 155:294–297.
8. Engebrecht, J., K. H. Nealson and M. Silverman. 1983. Bacterial biolumnecense; isolation and genetic analysis of the functions from *Vibrio fischeri*. Cell. 32:773–781.
9. Fuqua, W. C. and S. C. Winans 1994. A LuxR-LuxI type regulatory system activates Agrobacterium Ti plasmid conjugal transfer in the presence of a plant tumor metabolite. J. Bacteriol. 176:2796–2806.
10. Fuqua, W. C. S. C. Winans and E. P. Greenberg. 1996. Census and consensus in bacterial ecosystems: the LuxR-LuxI family of quorum sensing transcriptional regulators. Annu. Rev. Microbiol. 50:727–751.
11. Gilson, L. A. Kuo and P. V. Dunlap. 1995. AinS and a new family of autoinducer synthesis proteins. J. Bacteriol. 177:6946–6951.
12. Gray, K. M. and E. P. Greenberg, 1992. Physical and functional maps of the luminescence gene cluster in an autoinducer-deficient *Vibrio fischeri* isolated from a squid light organ. J. Bacteriol. 174:4384–4390.
13. Hanzelka, B. A. and E. P. Greenberg. 1995. Evidence that the N-terminal region of *Vibrio fischeri* LuxR protein constitutes and autoinducer binding domain. J Bacteriol. 177:815–817.
14. Hanzelka, B. A. and E. P. Greenberg. 1996. Quorum sensing in *Vibrio fischeri*: evidence that S-adenosyl methionine is the amino acid substrate for autoinducer synthesis. J. Bacteriol. 178:5291–5294.
15. Huisman, G. W. and R. Kolter. 1994. Sensing starvation: a homoserine lactone dependent signaling pathway in *Escherichia coli*. Science. 265:537–539.
16. Kaplan, H. B. and E. P. Greenberg. 1985. Diffusion of an autoinducer is involved in regulation of *Vibrio fischeri* luminescence system. J. Bacteriol. 163:1210–1214.
17. Kuo, A., N. V. Blough and P. V. Dunlap. 1994. Multiple N-acyl-L-homoserine lactone autoinducers of luminescence in the marine symbiotic bacterium *Vibrio fischeri*. J. Bacteriol. 176: 7558–7565.
18. Latifi, A. M. Foglino, K. Tanaka P. Williams and A. Lazdunski. 1996. A hierarchical quorum-sensing cascade is *P. aeruginosa* links the transcriptional activators LasR and RhlR to expression of the stationary phase sigma factor RpoS. Mol. Microbiol. 21:1137–1146.
19. Latifi, A. et al. 1995. Multiple homologues of LuxR and LuxI control expression of virulence determinants and secondary metabolites through quorum sensing in *P. aeruginosa* PAO1. Mol. Microbiol. Rev. 17:333–344.
20. More et al. 1996. Enzymatic synthesis of a quorum sensing autoinducer through the use of defined substrates. 272: 1655–1658.
21. Ochsner, U. A., and J. Reiser. 1995. Autoinducer-mediated regulation of rhamnolipid biosurfactant synthesis in *Pseudomonas aeruginosa*. Proc. Natl. Acad. Sci. USA 92:6424–6428.
22. Passador, L., J. M. Cook, M. J. Gambello, L. Rust, and B. H. Iglewski. 1993. Expression of *Pseudomonas aeruginosa* virulence genes requires cell-to-cell communication. Science. 260:1127–1130.
23. Passador, L., K. D. Tucker, K. R. Guertin, M. P. Journet, A. S. Kende, and B. H. Iglewski. 1996. Functional analysis of the *Pseudomonas aeruginosa* autoinducer PAI.J. Bateriol. 178:5995–6000.
24. Pearson, J. P., K. M. Gray, L. Passador, K. D. Tucker, A. Eberhard, B. H. Iglewski, and E. P. Greenberger. 1994. Structure of the autoinducer required for expression of *Pseudonomas aeruginosa* virulence genes. Proc. Natl. Acad. Sci. USA. 91:197–201.
25. Pearson, J. P., E. C. Pesci, and B. H. Iglewski. 1997. Roles of *Pseudonomas aeruginosa* las and rhl quorum-sensing systems in control of elastase and rhamnolipid biosynthesis genes. J. Bacteriol. 179:5756–5757.
26. Pesci, E. C., and B. H. Iglewski. 1997. The chain of command in Pseudonomas quorum sensing. Trends in Microbiol. 5(4); 132–135.
27. Pesci, E. C., J. P. Pearson, P. C. Seed, and B. H. Iglewski. 1997. Regulation of las and rhl quorum sensing systems in *Pseudonomas aeruginosa*. J. Bateriol. 179:3127–3132.
28. Ruby, E. G., 1996. Lessons from a cooperative bacterial-animal association: the *Vibrio fischeri-Euprymna scolopes* light organ symbioses. Ann. Rev. Microbiol. 50:591–624.
29. Salmond, G. P. C., B. W. Bycroft, G. S. A. B. Stewart, and P. Williams. 1995. The bacterial 'engima': cracking the codes of cell—cell communication. Mol. Microbiol. 16:615–624.
30. Schaefer, A. L., D. L. Val, B. L. Hanzelka, J. E. Cronan, Jr., and E. P. Greenberg. 1996. Generation of cell-to-cell signals in quorum sensing: acyl homoserine lactone synthase activity of a purified *Vibrio fischeri* LuxI protein. Proc. Natl. Acad. Sci. USA 93:9505–9509.
31. Seed, P. C., L. Passador, and B. H. Iglewski. 1995. Activation of the *Pseudonomas aeruginosa* lasI gene by LasR and the Pseudonomas autoinducer PAI: an autoinduction regulatory hierarchy. J. Bacteriol. 177:654–659.
32. Sitnikov, D. M., J. B. Schineller, and T. O. Baldwin. 1995. Transcriptional regulation of bioluminescence genes from *Vibrio fischeri*. Mol. Microbiol. 17:801–812.
33. Stevens, A. M., K. M. Dolan, and E. P. Greenberg. 1994. Synergistic binding of the *Vibrio fischeri* LuxR transcriptional activator domain and RNA polymerase to the lux promoter region. Proc. Natl. Acad. Sci. USA 91:12619–12623.
34. Winson, M. K., M. Camara, A. Latifi, M. Foglino, S. R. Chlabra, M. Daykin, M. Bally, V. Chapon, G. P. C. Salmond, B. W. Bycroft, A. Lazdunski, G. S. A. B. Stewart, and P. Williams. 1995. Multiple N-acyl-L-homoserine lactone signal molecules regulate production of virulence determinants and secondary metabolites in *Pseudonomas aeruginosa*. Proc. Natl. Acad. Sci. USA 92:9427–9431.

The entire contents of all of the aforementioned references are expressly incorporated herein by reference.

Equivalents

Those skilled in the art will recognize, or be able to ascertain using no more than routine experimentation, many equivalents to the specific embodiments and methods described herein. Such equivalents are intended to be encompassed by the scope of the following claims.

What is claimed is:

1. A method for producing a highly soluble, highly active bacterial autoinducer synthase molecule comprising:
   introducing DNA into a bacterial host cell, wherein said DNA encodes a bacterial autoinducer synthase molecule comprising the amino acid sequence of SEQ ID NO: 1 or an active portion thereof, and wherein said bacterial cell and said autoinducer synthase molecule are from identical bacterial species;
   growing said host cell at a temperature sufficient to overexpress said bacterial autoinducer synthase molecule in highly soluble, highly active form; and
   isolating said bacterial autoinducer synthase molecule from an extract of said bacterial host cell, thereby producing a highly soluble, highly active bacterial autoinducer synthase molecule.

2. The method of claim 1, wherein the bacterial host cell is a gram negative bacterial host cell.

3. The method of claim 1, wherein the bacterial host cell is Pseudomonas aeruginosa.

4. The method of claim 1, wherein said bacterial autoinducer synthase molecule comprises the amino acid sequence of SEQ ID NO: 1.

5. The method of claim 1, wherein the said purity of the autoinducer synthase is in the range of from about 50% to about 100% pure.

6. A purified, highly soluble, highly active autoinducer synthase molecule produced by the method of claim 1.

7. The method of claim 1, wherein said bacterial host cell is grown at a temperature of about 20° C.

8. The method of claim 1, wherein said bacterial host cell is grown at a temperature of about 25° C.

9. The method of claim 1, wherein said bacterial host cell is grown at a temperature of about 30° C.

10. The method of claim 1, wherein said bacterial host cell is grown at a temperature of about 32° C.

11. The method of claim 1, wherein said autoinducer synthase molecule is selected from the group consisting of quorum sensing system autoinducer synthase molecules of Vibrio fiseheri, Vibrio harveyi, Pseudomonas aeruginosa, Pseudomonas aureofaceins, Agrobacterium tumefaciens, Erwinia caratovora, Erwinia stewardii, Rhizobium leguminosarum, Enterobacter agglomerans, Yersinia enterocolitica, Serratia liquiaciens, Escherichia coli and Aeromonas hydrophila.

12. The method of claim 11, wherein the autoinducer synthase molecule is a quorum sensing system autoinducer synthase molecule of *Pseudomonas aeruginosa*.

13. The method of claim 11, wherein the autoinducer synthase molecule is a quorum sensing system autoinducer synthase molecule of *Vibrio fischeri*.

14. The method of claim 1, wherein said autoinducer synthase molecule is selected from the group consisting of LuxI, AinS, LucM, LasI, RhlI, PhzI, TraI, CarI, HsII, EsaI, EagI, YenI, SwrI, and AhyI.

15. The method of claim 14, wherein the autoinducer synthase molecule is RhlI.

16. The method of claim 14, wherein said autoinducer synthase molecule is LasI.

17. The method of claim 14, wherein said autoinducer synthase molecule is LuxI.

18. The method of claim 14, wherein said autoinducer synthase molecule is AinS.

19. The method of claim 14, wherein said autoinducer synthase molecule is TraI.52.

20. The method of claim 1, further comprising purifying the autoinducer synthase molecule.

21. The method of claim 1, wherein the purity of the autoinducer synthase molecule is about 75% to about 100% pure.

22. The method of claim 1, wherein the purity of the autoinducer synthase molecule is from about 85% to about 100% pure.

23. The method of claim 1, wherein the purity of the autoinducer synthase molecule is about 95% pure.

24. The method of claim 1, wherein said DNA encodes an autoinducer synthase molecule have amino acids 24–104 of SEQ ID NO. 1.

25. The method claim 1, wherein said DNA encodes an autoinducer synthase molecule having amino acids 24–73 of SEQ ID NO. 1.

26. The method of claim 1, wherein said DNA encodes an autoinducer synthase molecule having amino acids Arginine 24, Glutamic Acid 46, Aspartic Acid 48 and Glutamic Acid 101 of SEQ ID NO. 1.

27. The method of claim 1, wherein said autoinducer synthase molecule comprises less than 10% insoluble protein.

28. The method of claim 1, wherein said highly soluble, highly active autoinducer synthase molecule produced has a specific activity of about 21.7 to about 2,064 units/mg of autoinducer synthase molecule.

29. The method of claim 1, wherein said highly soluble, highly active autoinducer synthase molecule produced has a specific activity of about 2,064 units/mg of autoinducer synthase molecule.

30. A purified, highly soluble, highly active autoinducer synthase molecule comprising amino acids 24–104 of SEQ ID NO. 1.

31. The purified, highly soluble, highly active autoinducer synthase molecule of claim 30 having an amino acid sequence comprising amino acids 24–73.

32. The purified, highly soluble, highly active autoinducer synthase molecule of claim 30 having an amino acid sequence comprising Arginine 24, Glutamic Acid 46, Aspartic Acid 48 and Glutamic Acid 101.

* * * * *

UNITED STATES PATENT AND TRADEMARK OFFICE
CERTIFICATE OF CORRECTION

PATENT NO. : 6,723,321 B2
DATED : April 20, 2004
INVENTOR(S) : E. Peter Greenberg et al.

It is certified that error appears in the above-identified patent and that said Letters Patent is hereby corrected as shown below:

Column 1,
Line 3, insert
-- Government Support
    This work was supported by the National Institute of Health Grant Numbers AI15650 and GM18740 and the National Science Foundation (MCB-9808308). The government has certain rights in the invention. --

Column 24,
Line 66, replace "Serratia liquiaciens" with -- Serratia liquifaciens --

Column 25,
Line 9, replace "Phzl, Tral, Carl, Hsll, Esal" with -- Phzl, Tral, Carl, Hsll, Esal --
Line 32, replace "molecule have amino acids" with -- molecule having amino acids --

Signed and Sealed this

First Day of February, 2005

JON W. DUDAS
*Director of the United States Patent and Trademark Office*

SEQUENCE LISTING

<160> NUMBER OF SEQ ID NOS: 1

<210> SEQ ID NO 1
<211> LENGTH: 200
<212> TYPE: PRT
<213> ORGANISM: Pseudomonas aeruginosa

<400> SEQUENCE: 1

```
Met Ile Glu Phe Leu Ser Glu Ser Leu Glu Gly Leu Ser Ala Ala Met
 1               5                  10                  15

Ile Ala Glu Leu Gly Arg Tyr Arg His Gln Val Phe Ile Glu Lys Leu
            20                  25                  30

Gly Trp Asp Val Val Ser Thr Ser Arg Val Arg Asp Gln Glu Phe Asp
        35                  40                  45

Gln Phe Asp His Pro Gln Thr Arg Tyr Ile Val Ala Met Gly Arg Gln
    50                  55                  60

Gly Ile Cys Gly Cys Ala Arg Leu Leu Pro Thr Thr Asp Ala Tyr Leu
65                  70                  75                  80

Leu Lys Glu Val Phe Ala Tyr Leu Cys Ser Glu Thr Pro Pro Ser Asp
                85                  90                  95

Pro Ser Val Trp Glu Leu Ser Arg Tyr Ala Ala Ser Ala Ala Asp Asp
            100                 105                 110

Pro Gln Leu Ala Met Lys Ile Phe Trp Ser Ser Leu Gln Cys Ala Trp
        115                 120                 125

Tyr Leu Gly Ala Ser Ser Val Val Ala Val Thr Thr Thr Ala Met Glu
    130                 135                 140

Arg Tyr Phe Val Arg Asn Gly Val Ile Leu Gln Arg Leu Gly Pro Pro
145                 150                 155                 160

Gln Lys Val Lys Gly Glu Thr Leu Val Ala Ile Ser Phe Pro Ala Tyr
                165                 170                 175

Gln Glu Arg Gly Leu Glu Met Leu Leu Arg Tyr His Pro Glu Trp Leu
            180                 185                 190

Gln Arg Thr Leu Ser Met Ala Val
        195                 200
```